United States Patent
Mastrippolito et al.

(10) Patent No.: US 6,225,631 B1
(45) Date of Patent: May 1, 2001

(54) NON-INVASIVE RADIO-IMAGING ANALYSIS, IN PARTICULAR FOR EXAMINING SMALL ANIMALS IN VIVO, AND METHOD FOR USING SAME

(75) Inventors: Roland Mastrippolito, Montigny le Bretonneux; Lydie Ploux, Linas; Yves Pierre Charon, Gif-sur-Yvette; Laurent Pinot, Lardy; Luc Valentin, Bures-sur-Yvette; Alejandro Anibal Valda Ochoa, Orsay; Rainer Siebert, Port Marly; Philippe Laniece, Paris; HervéTricoire, Palaiseau, all of (FR)

(73) Assignee: Centre National de la Recherche Scientifique (CNRS), Paris (FR)

( * ) Notice: Subject to any disclaimer, the term of this patent is extended or adjusted under 35 U.S.C. 154(b) by 0 days.

(21) Appl. No.: 08/981,387
(22) PCT Filed: Jun. 19, 1996
(86) PCT No.: PCT/FR96/00945
§ 371 Date: Apr. 13, 1998
§ 102(e) Date: Apr. 13, 1998
(87) PCT Pub. No.: WO97/01108
PCT Pub. Date: Jan. 9, 1997

(30) Foreign Application Priority Data

Jun. 20, 1995 (FR) .................................................. 95 07345

(51) Int. Cl.$^7$ ...................................................... G01T 1/29
(52) U.S. Cl. ................. 250/363.02; 250/363.08; 250/363.1; 250/366
(58) Field of Search .................. 250/366, 363.1, 250/363.08, 363.02

(56) References Cited

U.S. PATENT DOCUMENTS

| | | | |
|---|---|---|---|
| 3,591,806 | * | 7/1971 | Brill et al. ............................. 250/366 |
| 4,395,635 | * | 7/1983 | Friauf et al. .......................... 250/366 |
| 5,245,191 | * | 9/1993 | Barber et al. .................... 250/363.04 |

FOREIGN PATENT DOCUMENTS

578679 * 5/1978 (SU) .................................... 250/366

* cited by examiner

*Primary Examiner*—Constantine Hannaher
(74) *Attorney, Agent, or Firm*—Blakely Sokoloff Taylor & Zafman

(57) ABSTRACT

A non-invasive analysis device including a plurality of sensors (110) combined with collimating structures (120) having a common source focus (O) and processing means (300) providing an AND-type combinational logic function of the output of the sensors (110) for sensing two coincidently transmitted beams that are at least slightly angularly correlated.

20 Claims, 6 Drawing Sheets

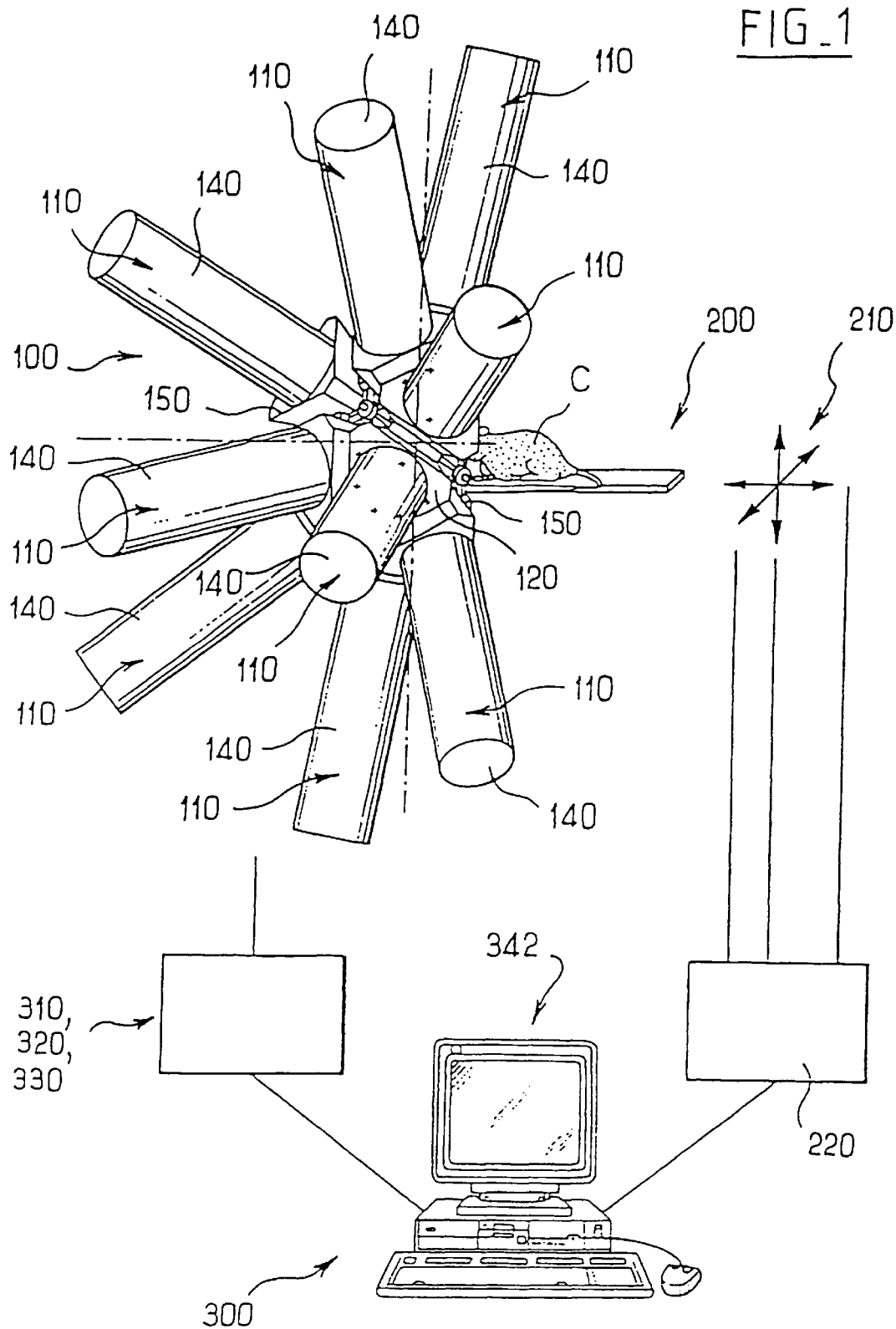
FIG_1

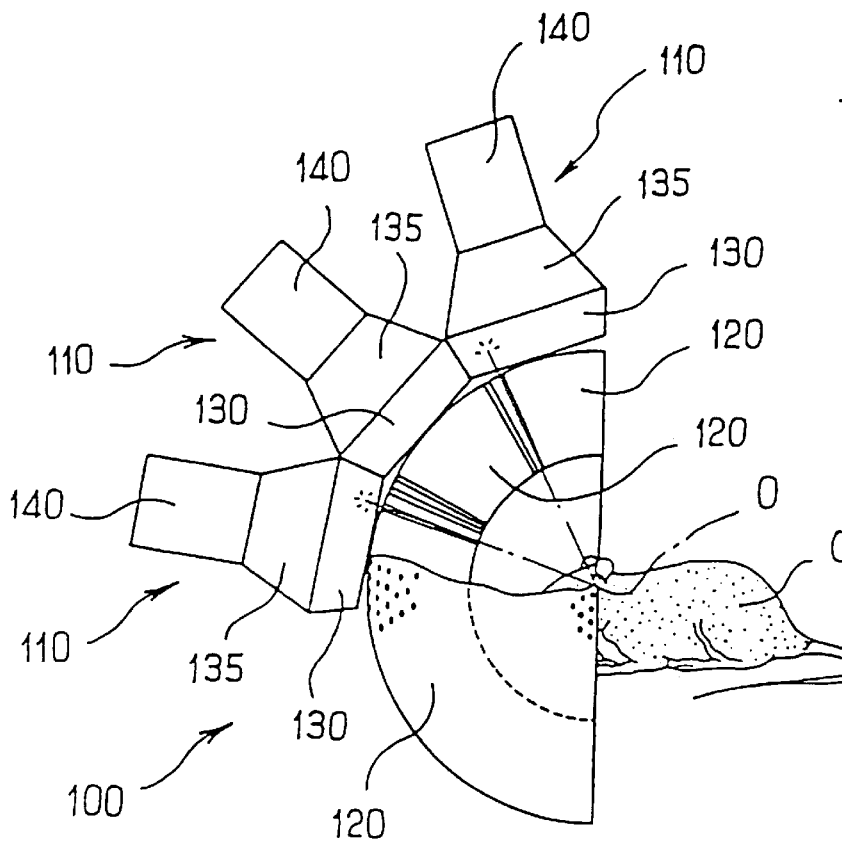
FIG_2
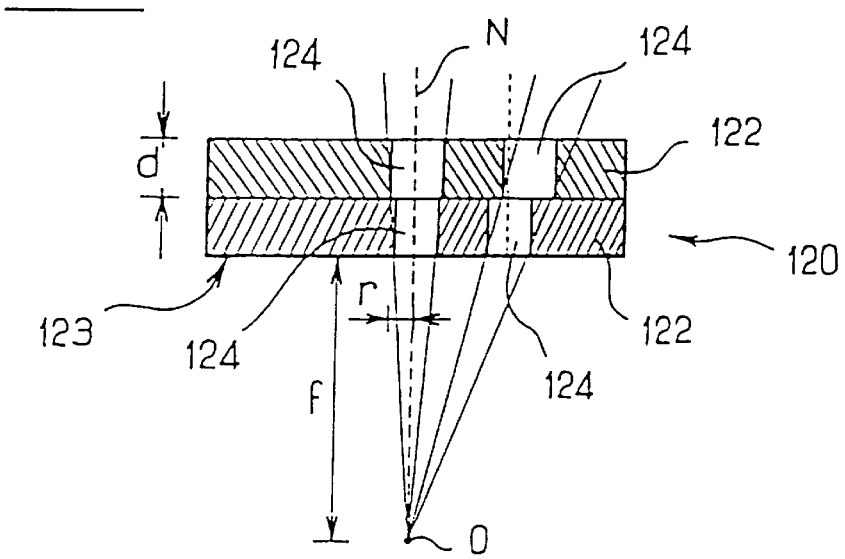
FIG_3

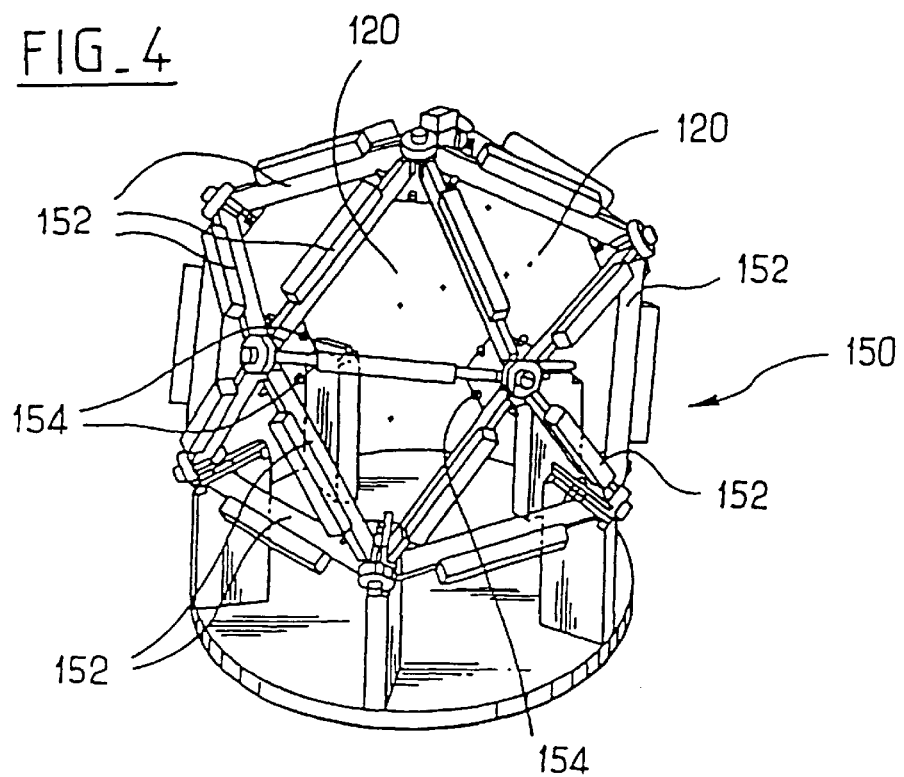
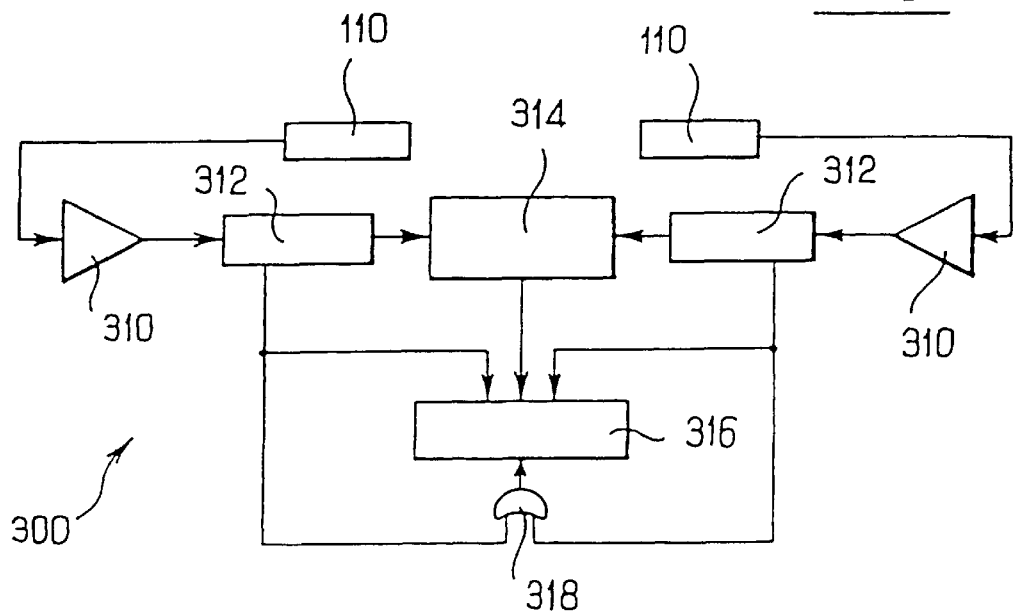

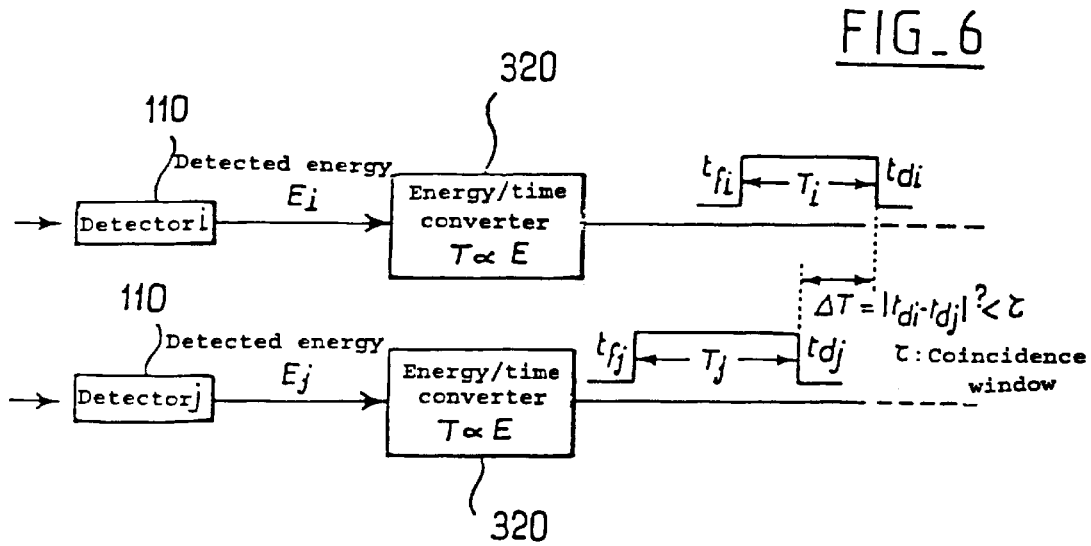
FIG_6

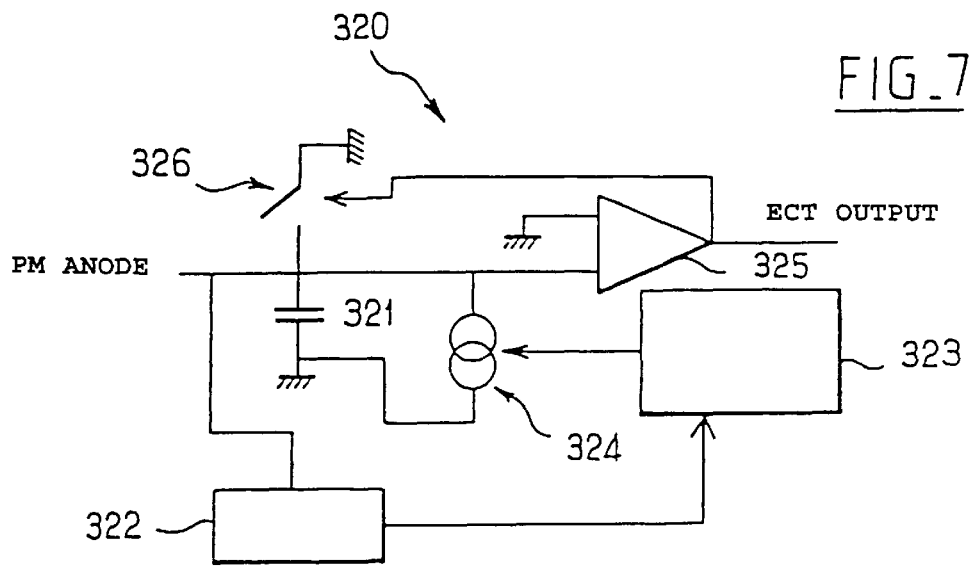
FIG_7
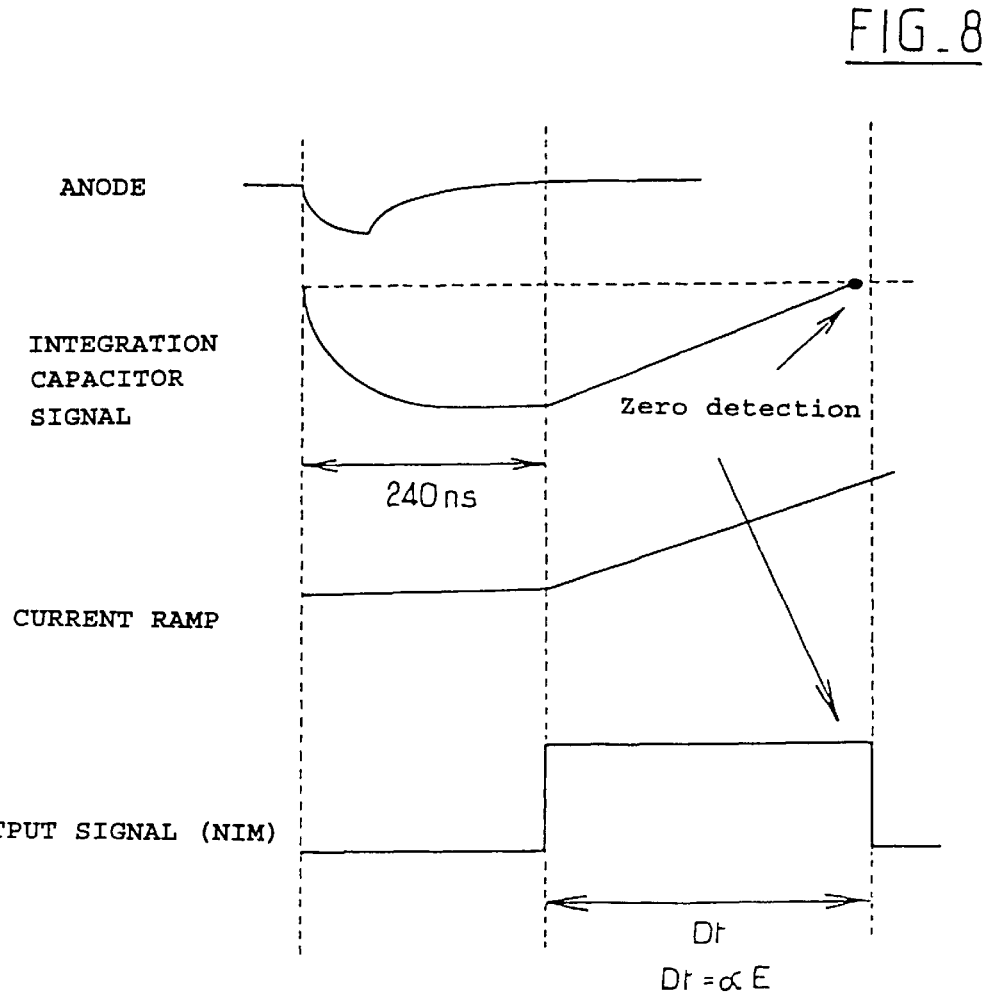
FIG_8

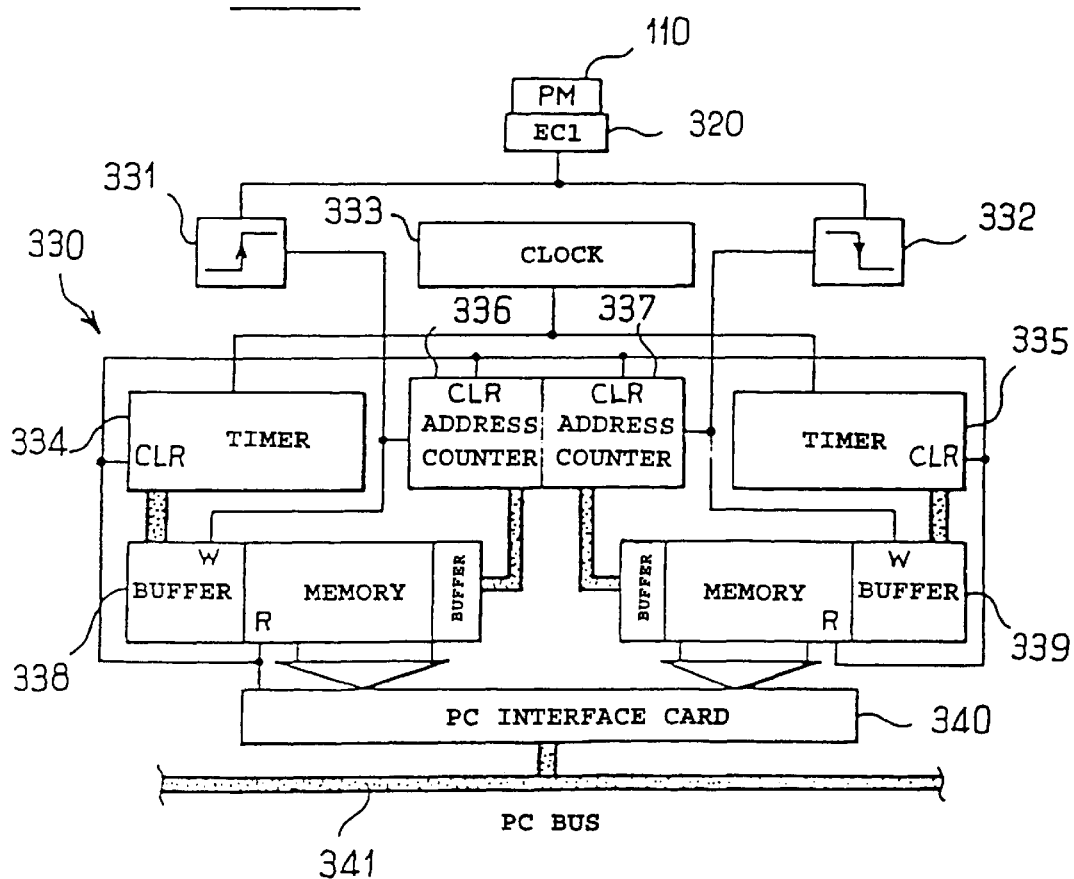

NON-INVASIVE RADIO-IMAGING ANALYSIS, IN PARTICULAR FOR EXAMINING SMALL ANIMALS IN VIVO, AND METHOD FOR USING SAME

The present invention relates to the field of non-invasive devices for analysis by radio-imaging.

Numerous analysis devices have already been proposed which use radioactive markers (Geiger counters coupled to a collimator, gamma cameras, etc.).

By utilizing the inherent property of radioactive marking which makes it possible to obtain quantitative information regarding the distribution of the tracer, radio-imaging techniques constitute an important tool both in the clinical field and in the field of fundamental research.

At present, the devices which are used most widely in this field belong to computer-aided emission tomography.

Computer-aided tomography has been developed along two different lines: the SPECT (Single Photon Emission Computed Tomography), which uses radio isotopes emitting a single photon by decay, for example $^{99m}$Tc, and the PET (Positron Emission Tomography) system, which uses radio isotopes in which two gamma radiation events are emitted simultaneously during the annihilation, in the tissue, of the positron produced by the decay of, for example, $^{18}$F.

Most SPECT systems are based on the use of one or more gamma cameras which are rotated about the object to be analyzed. A typical gamma camera consists of a multi-channel collimator, a large-area scintillator crystal, a light guide for optical coupling between the crystal and a set of photomultiplier tubes, and analog electronics for analyzing the amplitude of the signal and the position encoding. The entire device is contained within lead shielding in order to minimize the background noise produced by sources lying outside the field of view of the camera. The operating principle of a gamma camera is as follows: a photon, produced by a decay event in the by a center-of-gravity technique and to record and/or send it to a display device.

Positron emission tomography (PET) is another method which makes it possible to achieve in vivo and non-invasive regional measurement of physiological and metabolic parameters. Positron-emitter radioelements are isotopes having a surplus of protons with respect to their number of neutrons. When a positron is almost at rest, an encounter with an electron gives rise to an annihilation reaction which produces the simultaneous emission of two gamma photons departing in almost opposite directions. PET systems thus comprise an array of detectors in a ring which can detect the coincidence of two photons, as being indicative of the emission of the positron. The site of the annihilation then lies somewhere in the volume defined between the two detectors in question.

U.S. Pat. No. 4,288,697 describes a collimator formed by a stack of plates which are provided with perforations that correspond to a homothetic progression and are produced by chemical machining.

IEEE Transactions On Nuclear Science, Vol 41, no. 4, describes a conventional PET structure without a focusing collimating structure.

EP-A-0 289 737 describes a conventional scanner having a focal point.

Radio-pharmaceutical imaging constitutes an important tool in the diagnosis, characterization and treatment of diseases and functional disorders. However, before new pharmacological agents are used in man, it is generally necessary to characterize them in animal models in order to determine its biochemical, metabolic and physiological effects.

Of course, this characterization presupposes the availability of high-resolution imaging techniques in order to evaluate, ex vivo or in vivo, the spatial concentrations of the tracer which is injected.

At the present time, the spatial resolution of conventional tomographs is from 5 to 7 mm in the case of PET systems and from 8 to 12 mm in the case of SPECT systems. These values prove to be insufficient for carrying out studies in small animals, for example for rat studies of tumors, the typical size of which is of a few mm, or the distribution of neuroreceptors. In actual fact, it is necessary for a tomograph dedicated to the imaging of small animals to be able to provide spatial resolutions of at least ~2 mm.

Since 1990, a number of approaches based on PET and SPECT systems have been pursued in an attempt to achieve the desired performance.

However, these attempts at improvement have not yet been satisfactory, except at the cost of detection efficiency. The limitations of current tomographs in terms of resolution do not therefore allow in vivo studies to be extended to models on small animals, for which experimentation could be carried out more precisely.

The object of the present invention is to improve this situation.

This object is achieved according to the present invention by virtue of an analysis device comprising a plurality of detectors which are associated with collimating structures having a common source focus and detector output processing means, characterized in that the processing means perform a combinatorial logic function of the "AND" type on the output of the detectors in order to detect two coincidentally emitted radiation events that are at least slightly angularly correlated.

According to another characteristic of the invention, a multi-channel collimator is provided which is formed by a stack of plates having perforations, the thickness of the plates is less than the diameter of the perforations in the internal entry face of the collimator and the thickness of the span between the perforations is greater than the thickness of the plates.

According to an advantageous characteristic of the invention, the perforations in the plates are produced by chemical machining.

detecting these radiation events using a device of the aforementioned type.

Other characteristics, objects and advantages of the present invention will emerge when reading the following detailed description, and with reference to the appended drawings which are given by way of non-limiting example, and in which:

FIG. 1 represents a general schematic view of an analysis device according to the present invention, FIG. 2 represents a view, partially in section, of the detection part of this device, FIG. 3 schematically represents a stack of plates forming a collimator, FIG. 4 reprsents a structure for supporting of the detectors, FIG. 5 represents a partial diagram of the processing of an acquisition circuit according to a first variant of the invention, FIG. 6 schematically represents one form of energy/time conversion of the detected signals, according to a second variant of the invention, FIG. 7 represents a circuit diagram for this purpose, FIG. 8 represents time diagrams of the signals of this circuit, and FIG. 9 represents the general structure of an acquisition circuit.

The analysis device according to the present invention essentially comprises:
- a set of detectors 100,
- means 200 which are designed to support a body C to be analyzed and to allow a controlled relative displacement between it and the set of detectors 100, and
- processing means 300.

The set of detectors 100 comprises a plurality of detectors 110 focused on a common source focus O. The detectors 110 are carried by a support structure 150.

The detectors 110 preferably cover a solid angle at least equal to $2\pi$ steradians around the focus O.

According to the non-limiting particular embodiment represented in the appended figures, fifteen detectors 110 are provided, arranged in correspondence with fifteen adjacent faces of an icosahedron.

Each detector 110 preferably comprises:
- a collimator 120,
- a scintillator 130,
- an optical guide 135, and
- a photomultiplier 140.

A detector 110 of this type constitutes a counter of gamma and/or X radiation.

The collimators 120 are used to select the direction of the photons which are detected. They are formed by collimating structures that focus with large solid angle.

The focused collimation allows preferential detection of the radiation originating from a small region of space around the focal point O. A collimating structure of this type may be formed by a spherical cap with sectors or a polyhedron consisting of plane parts pierced with conical radial holes and constructed with a material having high photoelectric absorption power.

The conical radial holes preferably have at least substantially the same entry radii. They also preferably have at least substantially the same exit radii, the same vertex and are juxtaposed in a regular array with axial symmetry. The various channels are separated by partitions whose thickness is tailored to the energy of the radiation emitted by the source, so as to make it possible to absorb a high proportion of those protons whose trajectory is oblique with respect to the channel axis. In this way, only the photons emitted at the focal point will have a significant probability of reaching the scintillators 130.

In the scope of the present invention, as schematized in FIG. 3, the collimators 120 are preferably made by stacking perforated plates 122 having homothetic perforations 124.

The plates 122 are advantageously made of tungsten.

The reason for choosing tungsten is, on the one hand, its high absorption power: it has an absorption coefficient which is 30% to 40% greater than that of lead in the 10–500 keV range. Further, its mechanical properties ensure that the system is rigid and that the shape of the holes 124 is precise.

Moreover, within the scope of the invention, the homothetic perforations 124 made in the tungsten plates 122 are preferably obtained by chemical machining.

After lengthy studies and experiments, this technique was found to be superior to other known piercing techniques, such as laser piercing or wire spark erosion.

Machining by chemical etching consists in depositing a photosensitive resin on all the parts which are to be preserved, by making use of a mask representing the part to be produced. The part is then immersed in a bath which chemically etches the unprotected regions to form the desired openings 124.

As schematized in FIG. 3, the holes 124 in each plate 122 are cylinders that are parallel to one another and orthogonal to the faces of the plates 122. The result of this is that the solid angle, with respect to the source focus O, subtended by the aperture of a hole 124, decreases when moving away from the normal N to the plates 122 which passes through their homothetic center O.

The radius r of the holes 124 in the entry face 123, the thickness d of the plates 122 and the focal length f are determined so as to conserve an acceptable solid angle subtended by the aperture of each hole 124 with respect to O.

The thickness d of the plates 122 is preferably less than the diameter of the holes 124 in the internal entry face 123 of the collimator, for example equal to half this diameter, and the thickness of the span (septum) between the holes 124, in this internal face 123, is greater than or equal to the thickness of the plates 122 (i.e., for example, a distance between the centers of the holes to equal to three times the radius of the holes 124 on the internal face 123).

If the detectors 110 are assembled on a polyhedral support 150 of the regular icosahedron type, each collimation module 120 takes the form of a truncated triangular pyramid.

According to one non-limiting particular embodiment, each collimator 120 is formed by stacking 48 tungsten plates 122 having a thickness of 0.2 mm and an array of holes 124 defining a focal length f of the order of 7 cm, the holes 124 having, in the internal face 123 of the collimator, a radius of the order of 0.2 mm and an interaxial distance of the order 0.5 mm.

More precisely, each collimator 120 may be formed by stacking 24 different pairs of pairwise identical plates 122. In an arrangement of this type, each plate, of thickness d, is formed by juxtaposing two identical screens of thickness d/2. In this way, it is easy to produce holes 124 of diameter equal to d, with a separation between centers equal to 3d/2.

Yet more precisely, according to a non-limiting very particular embodiment, the radius of the holes 124 is 0.205 mm in the first plate 122 and 0.231 mm in the last plate 122, the distance between centers of the holes 124 is 0.614 mm in the first plate 122 and 0.693 mm in the last plate 122, the length of the edges of the first plate 122 is 87.2 mm and 98.3 mm for the last plate 122, and the distance to the focal point is 71.6 mm for the first plate 122 and 80.8 mm for the last plate 122.

The scintillator 130 is preferably formed by a single crystal of thallium-activated sodium iodide (NaI(Tl)).

In the case of an arrangement of the icosahedral type, the scintillator crystal has the form of a prism with triangular cross section in order to cover the entire exit surface of the collimator.

The light guide 135 provides optical coupling between each scintillator crystal 130 and the associated photomultiplier tube 140.

The structure 150 which supports the detectors 110 has to position the focal points of the collimators 120 with sufficient precision, typically of the order of 0.1 mm. There are a number of possible alternative embodiments for a support structure 150 of this type.

One particular embodiment, comprising a framework consisting of support bars 152 connected in sets of 5 by their ends and arranged along the edges of an icosahedron, is represented in FIG. 4. The plates 122 of the collimators 120 can be fixed on these bars 152 using rods 154 engaged in the corners of the plates 122.

However, as a variant, the structure 150 may support the light guides 135 of the detectors, instead of the collimators 120.

The system 200 for supporting and displacing the analyzed object is designed to define three degrees of freedom in linear displacement for the analyzed object C with respect to the sensors 110. These displacements can be brought about using three controlled and identified motorized shafts, schematically represented at 210 in FIG. 1, which are mutually orthogonal and associated with control means 220 which displace the motors interactively in order to position the object C and define an analysis region and a displacement step in order to automatically carry out the scan needed for acquisition.

The mechanism 210 for displacing each shaft may be composed of the following units for each motorized shaft:
  a translation table which drives the movement of a carriage by a screw/nut system, over a travel of, for example, 10 cm, and
  a stepper motor which allows controlled increments of, for example, 10 µm on each translation table.

The image resulting from an acquisition is constructed on the basis of the number of photons detected at each position of the displacement system 210. During the acquisition, it is therefore necessary to avoid any movement of the analyzed object C with respect to the displacement system 210, so as not to introduce artefacts in the image.

The system 200/210 consequently needs to be equipped with a system for specific positioning of the analyzed object.

By way of non-limiting example, in the case of imaging the brain of a rat, it is simply sufficient to immobilize the rat's head. The positioning system used in this case may correspond to those which are known in stereotaxy equipment. In this case, the head is immobilized at three points: at the entries of the auricular orifices, with two bars of adjustable position, and behind the incisors, with a bar on which the upper jaw bears.

The processing means 300 are designed to detect two temporally coincident radiation events produced on all of the detectors 110, without possibly taking into consideration coincidences produced in the same detector or those produced in diametrically opposite detectors.

An event is thus detected with all the more probability that it originates from the focal point by virtue of the combination of physical collimation, given by the collimating structure, and electronic collimation, given by the coincident detection of the photons produced by the decay.

When two photons of equal energy are to be detected, the processing and acquisition electronics 300 may be particularly simple, as represented in FIG. 5.

Each detection line associated with a detector 110 comprises an amplifier 310 and a discriminator module 312 which define a window around the photopeak. The outputs of the single-channel analyzers 312 are used to generate the coincidence signal in a time/amplitude converter 314. Three signals are sent to an interface card 316: the coincidence signal output by the converter 314 and the two outputs of the single-channel analyzers 312, in the latter case with the object of constructing a single-photon image for each detector 110. An acquisition signal, generated by logic combination in a gate 318 of the single-event images originating from the discriminators 312, is also applied to the interface card 316.

The device which has been described above and is illustrated in FIG. 5 nevertheless soon becomes bulky and impractical when the intention is for coincident detection, and from more than two detectors 110, of two radiation events of different energy.

In order to resolve this difficulty, a specific acquisition device is proposed in the scope of the invention, which makes it possible, for each detected event, to extract the energy of the event and the time at which is occurs, in order to test its temporal coincidence with another event.

A device of this type carries out, for example, energy/time conversion and encodes the events in a signal whose width is proportional to their energy. A system of this type also permits intrinsic encoding of the time of arrival of each event, and therefore permits coincidence tests.

The operating principle of a system for detecting coincidences which is based on an energy/time converter is as follows. Two events are detected on the detectors i and j respectively. Each energy/time converter produces a signal whose width T is proportional to the energy imparted to the detector. If the widths Ti and Tj correspond to the energies involved, the events are considered to be coincident if the difference between the start of the signal, $t_{di}-t_{dj}$, is less than the width of the coincidence window τ fixed beforehand.

FIG. 7 represents an illustrative embodiment of a circuit 320 according to the invention, which can perform energy/time conversion of this type, and FIG. 8 represents time diagrams of the signals taken from various points in the circuit.

The circuit in FIG. 7 comprises:
  a capacitor 321 capable of integrating the signal output by a photomultiplier 140,
  an output signal detector 322 for the photomultiplier,
  a delay cell 323 initiated by the aforementioned detector 322,
  a current source 324 which is connected in parallel with the capacitor 321 and is driven by the output of the delay cell 323,
  a comparator 325, one input of which is grounded and the other input of which is connected to the capacitor 321, the output of this comparator 325 constituting the output of the energy/time conversion device, and
  a switch 326 which is controlled by the comparator 325 and can discharge the capacitor 321.

This circuit 320 operates as follows.

The scintillation light produced by the interaction of an X or a γ photon in the NaI(Tl) crystal 130 is manifested, on the anode of the photomultiplier 140, as a signal having a very fast rise (in absolute value) followed by a virtually exponential fall, typically with a time constant of the order of 230 ns. Since the integral of this response is proportional to the energy imparted by the radiation to the crystal, the object of the energy/time converter 320 is to recover this integral in order to modulate the width of a square-wave signal. The integral of the anode signal is recovered on the capacitor 321 over a predefined time. This time is obtained on the basis of the delay applied to the signal extracted from the last dynode of the photomultiplier 140 (signal detection 322 and delay cell 323 modules). At the end of the integration time, the current generator 324, which is connected in parallel with the capacitor 321, is turned on in order to bring about a linear discharge of this capacitor. At the same time as the current generator 324 is started, the output of the flip-flop 325 which gives the output signal of the converter 320 changes to a logic state "1". Wherein the voltage of the capacitor 321 passes through zero, the flip-flop 325 returns to its low state, thus interrupting the high level of the output signal, the current generator 324 is stopped and the capacitor 321 is discharged fully by operating the switch 326.

FIG. 9 illustrates an illustrative embodiment of an acquisition circuit 330 according to the embodiment.

This circuit 330 is designed to encode energies which, for example, range from ~10 keV (27 keV for $^{123}$I and $^{125}$I) to ~300 keV (245 keV for $^{111}$In) at a maximum counting rate of ~$10^4$ hits per second per detector.

The system 330 is, for example, composed of:
- a set of (for example 15) detectors (scintillator 130+ photomultiplier 140),
- one energy/time converter 320 coupled to each detector 110,
- two detectors 331, 332, respectively for leading and trailing edges of the signals output by the converters 320,
- a clock 333 for the time base of the signals,
- two timers 334, 335 driven by the clock 333,
- two address counters 336, 337 driven by the edge detectors 331, 332, and
- two memories 338, 339 for cyclically and temporarily storing information then transferring it on to the bus 341 of a computer 342.

At the output of each energy/time converter 320, a signal is found whose width is proportional to the energy imparted to the detector 110. This width may, for example, vary from ~10 ns for 3 keV to ~1 µs for 300 keV. This readily permits a counting rate of $10^5$ hits per second. The times of the leading and trailing edges of the signal are calculated using the timers 334, 335 and clock 333, and are stored in the independent memories 338, 339. Once acquisition has been completed in a voxel, the data in the memories 338, 339 are transferred to the bus 341 of the PC in order to be processed using specific software.

Of course, the data acquisition method according to the present invention, with a view to imaging, comprises the initial step of injecting the body C to be analyzed with a radioactive marker capable of emitting two coincident radiation events that are at least slightly angularly correlated.

There are a number of possible variants for a marker of this type.

Attention may be drawn to at least three mechanisms of radioactive de-excitation which give rise to the emission of two coincident photons that are only slightly angularly correlated.

In the first of the de-excitation mechanisms (isobaric de-excitation of the nucleus), the decay of a parent nucleus produces an excited nucleus which changes to its ground state through a cascade, thus producing two coincident gammas. An example of a radioelement which de-excites by this mechanism is $^{111}$In. After an electron capture, $^{111}$In (half-life: 2.8 days), changes essentially to the 417 keV excited level of $^{111}$Cd. The ground state of $^{111}$Cd is reached by the cascade emission of one gamma of 171 keV followed by another with 245 keV; the half-life of the 245 keV level is 85 ns.

The other two mechanisms relate to radioelements whose decay starts with electron capture, and this serves to provide the first photon of the coincident pair. Specifically, in electron capture, the $X_k$ emission resulting from the rearrangement of the inner electron shells is utilized to provide a first photon. The deexcitation of the daughter nucleus gives rise to the second photon, and there are two possible ways that this may take place. If the de-excitation is radiative, there will be a γ photon coincidence with the $X_k$ photon. If the de-excitation takes place through internal conversion, there will also be electron rearrangement and emission of an $X_k$ photon in coincidence with that of the electron capture. Two isotopes of iodine (Z=53) give an example of these two coincidence mechanisms: $^{123}$I (half-life: 13 h) and $^{125}$I (half-life: 60 days). In both cases, the emitted $X_k$ radiation has an energy of about 27 keV, the probability of capturing an electron in the K shell is 80% and the fluorescence efficiency is 86%. In the case of $^{123}$I, the electron capture leads to an excited state of $^{123}$Te, which changes to the ground state by emitting a 159 keV gamma, the $X_k$-γ coincidence factor is about 70%. In the case of $^{125}$I, the excited state of the daughter nucleus at an energy of 35 keV, and the change to the ground state takes place either by emission of a gamma (7% probability) or by internal conversion; the coincidence factor for $X_k$-γ plus $X_k$-$X_k$ is 60%.

The invention is not limited to the use of the aforementioned radioelements: $^{123}$I, $^{125}$I and $^{111}$In, but extends to any other equivalent radioelement which can emit at least two temporarily coincident radiation events, for example γ-γ, γ-X or X-X, that are at least slightly angularly correlated.

After or before the radio tracer is injected, the body C to be analyzed is placed in the collimating detection structure 100.

The radiation events which are emitted by the object C and pass through the collimators 120 are detected by all the detectors 110 (scintillators 130+photomultipliers 140). The signal which is output by the detectors 110 and has been amplified and processed in the means 310, 320, 330 is sent to a computer 342 whose task is to acquire and store it. The processing electronics 310, 320, 330 deliver either the signals indicating coincidence between any two detectors 110, or a set of signals so that the coincidences which occur can be recovered a posteriori.

The coincidence detection makes it possible to optimize the spatial resolution and to reject signals originating from points lying outside the focal point.

Displacing the focal point of the collimators 120 by scanning through the volume of the region of interest during the acquisition makes it possible to construct the image of the object C voxel by voxel. It is thus unnecessary to use an algorithm for reconstructing the image, which may in particular amplify the statistical fluctuations on the reconstructed image, as in the case of the SPECT and PET techniques, and the image may, according to the invention, be displayed voxel by voxel as the acquisition proceeds.

The present invention may give rise to a number of applications which require measurement of the concentration of radioactively marked chemical species, non-limiting examples which may be mentioned of which applications include the in vivo examination of small animals, in particular within the scope of clinical research, relating for example to the detection of cardiovascular lesions, oncology, the detection and monitoring of tumors, studying the distribution of neuroreceptors, displaying the functions of the brain (in the case of neurodegenerative diseases, such as Parkinson's or Alzheimer's diseases, or Huntington's disease; or in the event of psychiatric disorders, such as in schizophrenia), gene therapy or, more generally, neurobiology or neuropharmacology in order to evaluate the effectiveness of treatments based on the administration of neuroprotective agents and on neural grafting.

The present invention is not, of course, limited to the particular arrangements which have just been described, but extends to any variant in accordance with its spirit.

The use of the device and the implementation of the method which were described above can be carried out by any authorized individual without requiring particular knowledge in the medical field.

What is claimed is:

1. Device for non-invasive analysis by radio-imaging of a body receiving a marker which can generate two coincidentally emitted radiation events that are not angularly correlated, comprising a plurality of detectors supported in non-coplanar directions for covering a spatial field around the body, the detectors being associated with respective collimating structures having a common source focus and detector output processing means wherein the processing means comprise means sensitive to the output of each one of the plurality of detectors and are able to check detection of emitted radiation events on any whatever two detectors of the plurality of detectors, in a specific deadline, so as to perform a combinatorial logic function of the "AND" type on the output of the detectors in order to detect two coincidentally emitted radiation events that are not angularly correlated generated by the marker.

2. Device according to claim 1, characterized in that it comprises means for counting radioactive radiation events.

3. Device according to claim 1, characterized in that it further comprises means which are designed to support the body to be analyzed, and to allow a controlled relative displacement between the body and the plurality of detectors.

4. Device according to claim 1, characterized in that the plurality of detectors cover a spatial field at least equal to $2\pi$ steradians around the focus.

5. Device according to claim 1, characterized in that the plurality of detectors are arranged in accordance with the faces of an icosahedron.

6. Device according to claim 1, wherein the plurality of detectors comprises fifteen detectors.

7. Device according to claim 1, characterized in that each of the plurality of detectors comprises a collimator, a scintillator, an optical guide and a photomultiplier.

8. Device according to claim 1, characterized in that each collimating structure comprises conical radial holes.

9. Device according to claim 1, further comprising a structure which is intended to support the plurality of detectors and is in the form of a framework consisting of bars connected by their ends.

10. Device according to claim 1, characterized in that it comprises means which can effect a relative displacement which is controlled and identified on the basis of three orthogonal axes between the body to be analyzed and the plurality of detectors.

11. Device according to claim 1, comprising processing means comprising energy/time conversion means which can encode the detected events in the form of signals whose width is proportional to the energy of the event.

12. Device according to claim 11, characterized in that the processing means comprise:
    a capacitor capable of integrating the signal output by a photomultiplier,
    an output signal detector for the photomultiplier,
    a delay cell initiated by the aforementioned detector,
    a current source which is connected in parallel with the capacitor and is driven by the output of the delay cell,
    a comparator, one input of which is grounded and the other input of which is connected to the capacitor, the output of this comparator constituting the output of the energy/time conversion means, and
    a switch which is controlled by the comparator and can discharge the capacitor.

13. Device according to claim 11, characterized in that the processing means comprises timers which are driven by a clock and are designed to define the trip times of the signal output by the energy/time conversion means.

14. Device according to claim 13, characterized in that the timers are controlled by detectors of leading and trailing edges of the signals output by the energy/time conversion means.

15. Device non-invasive analysis by radio-imaging of a body receiving a marker which can generate two coincidentally emitted radiation events that are not angularly correlated, comprising a plurality of detectors supported in non-coplanar directions for covering a spatial field at least equal to $2\pi$ steradians around the body, said detectors being associated with respective collimating structures having a common source focus and detector output processing means wherein the processing means comprises means sensitive to the output of each one of said plurality of detectors and are able to check detection of emitted radiation events on any whatever couple of two detectors belonging to said plurality of detectors, in a specific deadline, so as to perform a combinatorial logic function of the "AND" type on the output of the detectors in order to detect two coincidentally emitted radiation events that are not angularly correlated generated by said marker.

16. Device for non-invasive analysis of radio-imaging of a body receiving a marker which can generate two coincidentally emitted radiation events that are not angularly correlated, comprising a plurality of detectors supported in accordance with the faces of an icosahedron in non-coplanar directions for covering a spatial field at least equal to $2\pi$ steradians around the body, said detectors each comprising a collimator, a scintillator, an optical guide and a photomultiplier, said collimators having a common source focus and detector output processing means, wherein the device further comprises means which are designed to support the body to be analyzed and to allow a controlled relative displacement between the body and the plurality of detectors and wherein the processing means comprises means sensitive to the output of each one of said plurality of detectors and are able to check detection of emitted radiation events on any whatever couple of two detectors belonging to said plurality of detectors, in a specific deadline, so as to perform a combinatorial logic function of the "AND" type on the output of the detectors in order to detect two coincidentally emitted radiation events that are not angularly correlated generated by said marker.

17. Method for non-invasive analysis by radio-imaging, characterized in that it comprises the steps consisting in:
    injecting, into a body to be analyzed, a marker which can generate two coincidentally emitted radiation events that are not angularly correlated, and
    detecting these radiation events using an analysis device comprising a plurality of detectors which are associated with collimating structures having a common source focus and processing means performing a combinatorial logic function of the "AND" type on the output of the detectors in order to detect two coincidentally emitted radiation events that are not angularly correlated.

18. Method according to claim 17, characterized in that the marker which is used is designed to emit two coincidentally emitted radiation events that are at least slightly angularly correlated through atomic (X emitted following electron capture or internal conversion) or nuclear origin (gamma emitted during the isobaric de-excitation of a nucleus).

19. Method according to claim 17, characterized in that the marker which is used is chosen from the group comprising $^{123}$I, $^{125}$I, $^{111}$In.

20. Method according to claim 17, characterized in that the image of the body to be analyzed is constructed voxel by voxel.

* * * * *